US006815562B2

(12) United States Patent
Kunz et al.

(10) Patent No.: US 6,815,562 B2
(45) Date of Patent: Nov. 9, 2004

(54) PROCESS FOR THE PREPARATION OF NITRODIPHENYLAMINES

(75) Inventors: Klaus Kunz, Düsseldorf (DE); Joachim Haider, Köln (DE); Dirk Ganzer, Leverkusen (DE); Ulrich Scholz, Mülheim (DE); Adolf Sicheneder, Hohenlockstedt (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/751,311

(22) Filed: Jan. 2, 2004

(65) Prior Publication Data

US 2004/0143138 A1 Jul. 22, 2004

(30) Foreign Application Priority Data

Jan. 7, 2003 (DE) ......................................... 103 00 125

(51) Int. Cl.[7] ............................................ C07C 209/10
(52) U.S. Cl. ........................ 564/406; 564/420; 564/421; 564/422; 564/423
(58) Field of Search ................................ 564/406, 420, 564/421, 422, 423

(56) References Cited

U.S. PATENT DOCUMENTS

| | | | |
|---|---|---|---|
| 4,187,248 A | 2/1980 | Merten et al. | 260/576 |
| 4,187,249 A | 2/1980 | Maender et al. | 260/576 |
| 4,665,232 A | 5/1987 | Podder et al. | 564/406 |
| 4,670,595 A | 6/1987 | Podder et al. | 564/406 |
| 4,683,332 A | 7/1987 | Sturm | 564/414 |
| 5,840,982 A | 11/1998 | Reynolds et al. | 564/423 |
| 6,316,380 B1 | 11/2001 | Nolan et al. | 502/155 |
| 6,316,673 B2 * | 11/2001 | Giera et al. | 564/423 |
| 6,362,357 B1 | 3/2002 | Nolan et al. | 558/44 |
| 6,369,265 B1 | 4/2002 | Nolan et al. | 560/102 |
| 6,403,802 B1 | 6/2002 | Nolan et al. | 548/103 |
| 6,586,599 B1 | 7/2003 | Nolan et al. | 546/259 |

FOREIGN PATENT DOCUMENTS

| | | |
|---|---|---|
| DE | 185663 | 4/1906 |
| DE | 32 46 151 | 6/1984 |

OTHER PUBLICATIONS

Organic Letters, (month unavailable) 2002, vol. 4, No. 4, pp. 581–584, "Copper–Catalyzed Coupling of Alkylamines and Aryl Iodides: An Efficient System Even in an Air Atmosphere" by F. Y. Kwong et al. Also See Supporting Information Attached.

Encyclopedia Of Chemical Technology, Fourth Edition, vol. 3, (month unavailable) 1992, pp. 424–456.

Ullmann's Encyclopedia Of Industrial Chemistry, Fifth, Completely Revised Edition, vol. A 3 (month unavailable) 1985, pp. 91–111.

Tetrahedron Letters 42, (month unavailable) 2001, pp. 4791–4793, "Formation of aryl–nitrogen Bonds using a soluble copper(I) catalyst" by R. Gujadhur et al.

* cited by examiner

*Primary Examiner*—Peter O'Sullivan
(74) *Attorney, Agent, or Firm*—Godfried R. Akorli; Diderico van Eyl; Jennifer R. Seng

(57) ABSTRACT

The present invention relates to a process for the preparation of nitrodiphenylamines by reaction of nitrohalogens with anilines, a base and a catalyst, and to a process for the preparation of aminodiphenylamine by hydrogenation of the nitrodiphenylamine intermediately prepared.

9 Claims, No Drawings

PROCESS FOR THE PREPARATION OF NITRODIPHENYLAMINES

FIELD OF THE INVENTION

The present invention relates to a process for the preparation of nitrodiphenylamines by reaction of nitrohalogens with anilines, a base and a catalyst, and to a process for the preparation of aminodiphenylamine by hydrogenation of the nitrodiphenylamine intermediately prepared.

BACKGROUND OF THE INVENTION

N-Substituted anilines are important intermediate products for the preparation of agricultural and fine chemicals.

As described in Kirk-Othmer, Encyclopedia of Chemical Technology, 4$^{th}$ edition, 1992, vol. 3, page 424–456 and in Ullmann's Encyclopedia of Industrial Chemistry, 5$^{th}$ edition, vol. A3, 1985, page 91–111, 4-aminodiphenylamine (4-ADPA) is an important precursor for the synthesis of anti-ageing agents and stabilizers in the rubber and polymers industry.

Hartwig describes in Angew. Chem., Int. Ed. 1998, 37, 2046–2067 and Buchwald in Top. Curr. Chem. 2002, 219, 131–209, that the synthesis of N-substituted anilines can also be carried out by coupling, catalyzed by transition metals, of activated chloro-, bromo- or iodoaromatics with primary or secondary amines, optionally in the presence of a palladium catalyst, a phosphane and a base.

WO-A2 01/66248 discloses that instead of the complex Pd-phosphane complexes, N-heterocyclic Pd-carbene complexes can also alternatively be employed.

The disadvantage of the syntheses described in the prior art cited above is the use of palladium, which is poorly available and subject to wide price variations, and is expensive to recover. The use of the phosphane ligands of the specifications cited in the prior art also presents problems because of their poor availability and their high toxicity.

DE-A 3 246 151, DE-A 3 501 698, DE-A 185 663, U.S. Pat. Nos. 4,670,595, 4,187,249, 4,683,332 and 4,187,248 disclose the preparation of N-substituted anilines from p-nitrochlorobenzene in the presence of an acid acceptor or a neutralizing agent with the aid of copper catalysts.

U.S. Pat. No. 5,840,982 reports that the first stage for the preparation of N-substituted anilines is usually carried out with copper catalysts, and the second with metal components which differ from these, e.g. nickel.

Venkatamaran et al. discloses in Tetrahedron Letters, 2001, 42, 4791–4793 that the preparation of triarylamines from diarylamines and iodoaromatics is possible in high yields with the aid of defined copper-phosphane complexes. Selective preparation of diarylamines, which are very important economically, is not described in this publication.

Buchwald et al. describes in Organic Letters, 2002, 4, 581–584 the general reaction of halogenobenzenes with anilines. The use of the catalyst according to formula (I) is not disclosed.

There was therefore the need to develop catalysts, which are-suitable in an advantageous manner for a process for the preparation of nitrodiphenylamines starting from aryl chlorides and aryl bromides.

Since aryl chlorides are usually significantly slower to react in nucleophilic aromatic substitution than aryl iodides, significantly more drastic conditions, such as high temperatures, must be chosen for such a reaction. This is in general accompanied by a significantly reduced selectivity of the reaction.

The object of the present invention is therefore to provide a process, which renders it possible to react nitrohalogenobenzenes with anilines to give nitrodiphenylamines in high yields and with a high selectivity.

SUMMARY OF THE INVENTION

The present invention is directed to a process for the preparation of nitrodiphenylamines, wherein nitrohalogenobenzenes are reacted with anilines, a base and a catalyst of the formula (I)

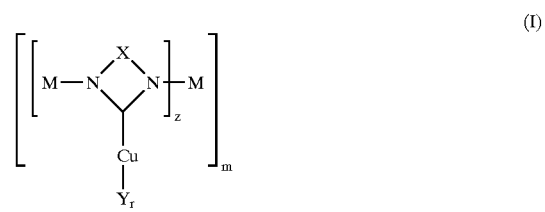

wherein
X is a 1,2-ethanediyl or 1,2-ethenediyl radical and
M can be identical or different and represents $C_1$–$C_{19}$-alkyl, $C_7$–$C_{19}$-aralkyl, $C_6$–$C_{18}$ aryl groups or $C_6$–$C_{19}$-heteroaryls having 1 to 3 nitrogen atoms, wherein two or more radicals M can be bridged in any desired manner by a covalent bridge or by an alkylidene bridge containing 1 to 4 carbon atoms or via an aryl or heteroaryl ring,
Y represents halogen or a trifluoroacetyl, trifluoromethanesulfonyl, nonafluorobutanesulfonyl, cyanide, acetyl, fluorinated acetylacetonyl, nitrate, arylsulfonyl, oxinate, phosphate, carbonate or tetrafluoroborate radical,
z represents 1, 2 or 3,
m represents integers from 1 to 6 and
r denotes 0, 1 or 2.

The base for the process according to the present invention can be chosen from the group consisting of bicarbonates, carbonates, methanolates, ethanolates, isopropylates, tert-butanolates, phosphates, fluorides, silazanes, hydrides and acetates of lithium, sodium, potassium and caesium.

The catalyst of the formula (I) can also be prepared in situ for the process according to the present invention.

The present invention also provides a process for the preparation of aminodiphenylamine, wherein the nitrodiphenylamine prepared by the process according to the present invention is hydrogenated, without isolation.

In the general formula (I)
X preferably represents a 1,2-ethenediyl group,
M preferably represents a $C_1$–$C_{12}$ alkyl group, $C_5$–$C_7$ cycloalkyl group, $C_6$–$C_{12}$-aryl group or a $C_5$–$C_{12}$ heteroaryl group having 1 to 3 nitrogen atoms in the ring, or represents a methyl group, which is bridged in any desired manner with another radical M by a covalent bridge or by an alkylidene bridge containing 1 to 4 carbon atoms or via an aryl or heteroaryl ring. $C_1$–$C_{12}$ alkyl groups are to be understood as meaning both branched and unbranched alkyl groups. Methyl, ethyl, n-propyl, i-propyl, n-butyl and tert-butyl are preferred. $C_5$–$C_6$ Cycloalkyl groups are preferably to be understood as meaning cyclopentyl and cyclohexyl groups. Phenyl, biphenyl or the naphthyl radical are preferably employed as $C_6$–$C_{12}$-aryl groups. Pyridyl or quinolyl radicals are the preferred $C_5$–$C_{12}$-heteroaryl radical having 1 to 3 nitrogen atoms.

Y preferably represents chlorine, bromine, iodine or a trifluoromethylsulfonyl or an acetonyl radical.

z preferably represents 1 or 2 m preferably represents 1, 2 or 3 r preferably represents 1 or 2

Copper compounds with a valency level of 0, +I or +II are preferably employed for the preparation of the catalysts. Preferred starting compounds for the catalysts include copper oxides, copper halides, copper cyanides and copper acetates, copper acetylacetonates in fluorinated or non-fluorinated form, copper nitrates, copper trifluoromethanesulfonates, copper arylsulfonates, copper oxinates and copper phosphates, more preferred are copper(I) chloride, copper(I) bromide, copper(I) iodide, copper(II) bromide, copper(II) chloride, copper(II) acetate, copper(II) oxide or copper(II) acetylacetonate, as well as copper powder. Copper(I) chloride, copper(I) bromide or copper(I) trifluoromethanesulfonate are most preferred.

Those catalysts which contain two symmetric, unsymmetric or two bridged ligands are preferred. Symmetric dialkylimidazolidenes, diarylimidazolidenes and diheteroarylimidazolidenes, unsymmetric arylalkylimidazolines and N-substituted imidazolidenes bridged via heteroaryls or alkylidene bridges are particularly preferred. N,N'-Dimethylimidazolidene, N,N'-dicyclohexylimidazolidene, N,N'-diphenylimidazolidene, N,N'-di(2,6-diisopropyl)phenylimidazolidene, N,N'-di(2,6-dimethyl)phenylimidazolidene, N,N'-di(2,4,6-trimethyl)phenylimidazolidene, N,N'-di(2-pyridyl)imidazolidene, N-benzyl-N'-methyl-imidazolidene and ligands which are formed by two-fold deprotonation of 1,3-bis[N-(N'-methyl)imidazoliummethyl]-5-methylbenzene dihalide, 2,6-bis-[N-(N'-methyl)-imidazoliummethyl]pyridine dihalide, 1,2-bis-[N-(N'-methyl)-imidazolium]-1,2-diphenylethane halide or bis-[N-(N'-methyl)imidazolium]-methane dihalide are very particularly preferred.

Preferred catalysts of the formula (I) include (N,N'-dimethylimidazolidene)-copper(II) bromide, (N,N'-dicyclohexylimidazolidene)-copper[II] bromide, [N,N'-di(2,4,6-trimethyl)phenylimidazolidene]-copper(II) bromide, [N,N'-di(2-pyridyl)imidazolidene]-copper[II] bromide, (N-benzyl-N'-methylimidazolidene)-copper[II] bromide, {1,3-bis-[N-(N'-methyl)imidazolidene-methyl]-5-methylbenzene}-copper[II] bromide, {1,3-bis-[N-(N'-methyl)imidazolidene-methyl]-5-methylbenzene}-copper[I] trifluoromethylsulfonate, {2,6-bis-[N-(N'-methyl)-imidazolidenemethyl]pyridine}-copper[II] bromide, {1,2-bis-[N-(N'-methyl)imidazolidene]-1,2-diphenylethane}-copper[II] bromide and {bis-[N-(N'-methyl)imidazolidene]methane}-copper[II] bromide. (N,N'-Dimethylimidazolidene)-copper(II) bromide and {1,3-[bis-(N-(N'-methyl)imidazolidenemethyl]-5-methyl-benzene}-copper[II] bromide are particularly preferred.

The catalysts mentioned can be employed either individually or in any desired mixture with one another. The most favorable mixture composition can be determined by appropriate preliminary experiments.

The catalysts of the formula (I) to be employed according to the present invention are prepared by deprotonation of ligands of the formula (II)

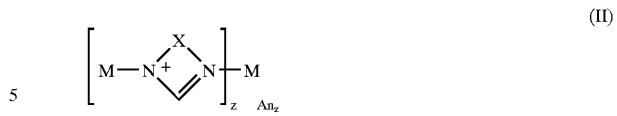

with a base and subsequent reaction with a copper compound of the formula (III)

wherein M, X, Y, z and r have the meaning given in the case of the formula (I).

Formula (II) is representative here of the possible tautomeric compounds, which are also included in the scope of the invention.

"An" is preferably an anion of an acid which has a pKa value of 3 or less than 3. "An" is more preferably hydrogen sulfate, chloride, bromide, iodide, tetrafluoroborate, hexafluorophosphate or one half of an equivalent of sulfate.

"An" is most preferably chloride, bromide or iodide.

Bases which are employed for the deprotonation of the ligand include alkali metal and/or alkaline earth metal alcoholates, hydrides and/or hydroxides. Preferred bases for the deprotonation of the ligands are sodium methanolate, potassium tert-butylate, potassium amylate, sodium hydride, potassium hydride, potassium hydroxide, sodium hydroxide and barium hydroxide. The deprotonation of the ligands preferably takes place by potassium tert-butylate.

The solvents for the deprotonation of the ligand are inert organic solvents. Ethers, such as diethyl ether and THF, and also toluene, xylene, chloroform, methylene chloride, methanol and/or ethanol are preferred, the deprotonation being carried out in the temperature range from –50 to 50° C. Preferably, the deprotonation is carried out in ethers at temperatures of between –35° and room temperature.

For the preparation of the catalysts of the formula (I), the starting substances of the formula (II) and of the formula (III) are employed in a molar ratio such that the desired target catalyst of the general formula (I) results. The molar ratio of the imidazolium salts of the formula (II) to the copper compounds of the formula (III) is preferably chosen in the range from 40:1 to 0.5:1, more preferably in the range from 5:1 to 1:1, most preferably in the range from 4:1 to 1:1.

The solvents required for the preparation of the catalysts are the same as those used for the deprotonation of the ligand. The most favorable amount of solvent to be employed can be determined by appropriate preliminary experiments. When the deprotonation is complete, the reaction temperature is increased to a temperature in the range from 10 to 30° C. The temperature is preferably increased to temperatures in the range from 15 to 25° C. in the course of 60 to 180 minutes.

The catalysts either can be added as an isolated compound to the process according to the present invention for the preparation of diarylamines, or can also be reacted in situ during the reaction of the substituted benzenes with the arylamines.

For the process according to the present invention, the catalysts are employed in amounts of 0.02 mol % to 10 mol %, preferably 0.1 mol % to 3 mol %, based on the amount of nitrohalogenobenzenes employed.

Nitrohalogenobenzenes are to be understood as meaning all nitrohalogenobenzenes which contain at least one halogen chosen from the group consisting of fluorine, chlorine and bromine. Preferred halogens are fluorine and chlorine. In addition to the halogen and the nitro group, the nitrohalogeno-=benzenes can also contain one or more substituents chosen from the group consisting of $C_1$–$C_{12}$-alkyl groups. The unsubstituted nitrohalogenobenzenes and nitroalkylhalogenobenzenes with unbranched alkyl groups are preferred. The nitrohalogenobenzenes and nitroalkylhalogenobenzenes in which the nitro group is in the para-, ortho- or meta-position relative to the halogen, preferably in the para-position, are more preferred. 4-Nitro-2-methylchlorobenzene, 4-nitro-3-methylfluorobenzene, 4-nitrochlorobenzene, 3-nitrochlorobenzene and 2-nitrochlorobenzene are most preferred. Of these, 4-nitrochlorobenzene is preferred.

In addition to aniline, all the o-, m- and p-substituted anilines known to the expert can also be employed in the process according to the present invention. Preferred substituents are branched or unbranched $C_1$–$C_{29}$-alkyl, $C_2$–$C_{29}$-alkenyl, $C_1$–$C_{29}$-acyl, $C_1$–$C_{29}$-alkylthio, $C_1$–$C_{29}$-alkylamino and $C_1$–$C_{29}$-alkoxy radicals, $C_1$–$C_{29}$ carboxylic acid esters having 1 to 29 C atoms in the carboxylic acid part and 1 to 29 C atoms in the ester part and sulfonic acid radicals having 1 to 9 carbon atoms in the ester part. Branched or unbranched alkyl, alkenyl or alkylthio groups with the numbers of carbon atoms mentioned, such as the methyl, n-butyl tert-butyl octyl, decyl, dodecyl, myristyl and stearyl group, are preferred. Preferred substituted anilines are vinylaniline, 4-tert-butylaniline, p-anisidine, o-anisidine, o-toluidine, p-toluidine, anthranilic acid methyl ester, o-aminobenzonitrile, p-aminobenzonitrile and 4-ethylaniline. Aniline is most preferred.

In the process according to the invention, in general 1 to 10 mol, preferably 1.5 to 8 mol, more preferably 2 to 6 mol of the corresponding aniline are employed per mol of nitrohalogenobenzene.

Bases which are employed in the process according to the present invention are alkali metal and/or alkaline earth metal carbonates, alcoholates, phosphates, fluorides and/or hydroxides, where potassium carbonate, sodium carbonate, caesium carbonate, caesium bicarbonate, sodium methanolate, potassium tert-butylate, potassium amylate, caesium fluoride, potassium phosphate and barium hydroxide are preferred. Potassium carbonate, sodium carbonate, caesium carbonate and/or caesium bicarbonate are more preferred. Potassium carbonate is most preferred.

The bases can be employed either in less than the stoichiometric or the stoichiometric amount or in an excess of up to ten times the equivalent amount with respect to the nitrohalogenobenzene. The bases are preferably employed in 0.3 to 2 equivalent amounts, based on the nitrohalogenobenzene.

It is of advantage for the process according to the present invention if the bases employed are pretreated by grinding and/or drying.

The grinding can be carried out in commercially available mills in the process according to the present invention. The grinding has the effect here of a drastic increase in the specific surface area, which leads to a significant increase in the conversion. In many cases an increase in the specific surface area by a factor of 10 to 20 is to be observed by the grinding.

After the grinding the specific surface areas of the bases are approx. 0.1 to 10 $m^2/g$, preferably 0.2 to 1 $m^2/g$ (BET).

Because of the pronounced hygroscopic properties of the bases employed in the process according to the present invention, the phosphates and carbonates above all tend towards a greater or lesser uptake of constituents from the atmosphere, such as water and carbon dioxide. At and above an uptake of approx. 30 per cent by weight of constituents from the atmosphere, a significant influence on the conversions to be achieved is detectable. In addition to grinding, drying of the bases is therefore often also necessary.

Drying of the bases is carried out here, depending on the nature of the base used, such that they are heated to temperatures of approx. 50 to 200° C., preferably 100 to 160° C., under a reduced pressure of approx. 0.01 to 100 mbar for several hours.

The process according to the present invention is preferably carried out by a procedure in which the base is first dried at temperatures in the range from 20 to 250° C., preferably at temperatures from 110 to 210° C., the temperature in the reaction vessel is cooled and the nitrohalogenobenzenes, anilines and the catalyst or, in the case where the catalyst is prepared in situ, the ligand according to formula II with the copper compound according to formula II are then added.

The process according to the present invention can be carried out either in the presence or in the absence of an additional suitable solvent. Inert organic hydrocarbons such as xylene and toluene, are preferred as the additional solvent. The aromatic amines employed can themselves furthermore function as the solvent.

The amount of solvents to be employed can easily be determined by appropriate preliminary experiments.

In order to increase the yield of nitrodiphenylamines, the water of reaction formed can be removed by distillation, as described in DE-A 2 633 811 and DE-A 3 246 151, by addition of a suitable entraining agent, such as benzene, toluene or xylene.

The process according to the present invention can be carried out in a continuous or discontinuous manner by the methods known to the expert.

The nitrodiphenylamines prepared by the process according to the present invention can be reduced to the corresponding aminodiphenylamines by a hydrogenation. The hydrogenation is carried out in the manner known to the expert with a reducing agent, such as hydrogen, during which the copper from the formula (I) already present does not have to be removed and optionally a suitably inert catalyst support.

It is of course also possible to carry out the hydrogenation in the presence of additional hydrogenation catalysts, such as those based on nickel, palladium or platinum. Suitable catalyst supports can also be used for these catalysts.

Suitable materials for use as the catalyst support include all the catalyst supports known to the expert based on carbon, element oxides, element carbides or element salts in various use forms. Examples of carbon-containing supports are coke, graphite, carbon black or active charcoals. Examples of the element oxide catalyst supports are $SiO_2$ — in the form of naturally occurring or synthetic silica and naturally occurring or synthetic quartz—$Al_2O_3$, preferably α- and γ-$Al_2O_3$, aluminas, preferably naturally occurring or synthetic alumosilicates, such as zeolites, laminar silicates, such as bentonite, montmorillonite, $TiO_2$, preferably in the rutile or anatas type, $ZrO_2$, MgO and ZnO. Examples of element carbides and salts are SiC, $AlPO_4$, $BaSO_4$ and $CaCO_3$. In principle, both synthetic materials and supports of natural sources, such as pumice, kaolin, bleaching earths, bauxites, bentonites, kieselguhr, asbestos or zeolites, can be used. Active charcoals and Si-, Al-, Mg-, Zr- and Ti-containing materials are preferably employed as the support materials. Active charcoal is more preferred.

The hydrogenation can of course also be carried out with other reduction methods, such as are known to the expert and are described in Reductions in Organic Chemistry, Second Edition, ACS Monograph 188.

For the hydrogenation, the nitrodiphenylamine can either be isolated, or the nitrodiphenylamine obtained from the process according to the present invention is hydrogenated directly, alkyl halides being removed, but without further working up.

The temperatures during the hydrogenation are approximately 0 to 200° C., preferably 40 to 150° C. The hydrogen pressures for the hydrogenation are 0.1 to 150 bar, preferably 0.5 to 70 bar, more preferably 1 to 50 bar.

The corresponding aminodiphenylamines are obtained by the process according to the present invention with a high selectivity (>95%) and yields of up to 97% of theory.

EXAMPLES

Example 1

Preparation of {1,3-bis-[N-(N'-methyl)imidazolidene-methyl]-5-methylbenzene}-copper[II] bromide, $C_{17}H_{20}Br_2CuN_4$ (× 2KBr)

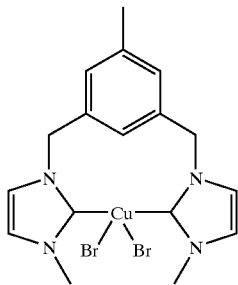

The bisimidazolium salt (135 mg, 0.31 mmol) is dissolved in 10 ml toluene under an argon atmosphere, and potassium tert-butylate (71 mg, 0.63 mmol) is added at 0° C. After 2 h copper(II) bromide (70 mg, 0.31 mmol) is added and the mixture is stirred for a further 12 h. The solvent is then removed in vacuo, and the product is obtained as a pale powder.

FD/MS: 343 (M–2Br, main component), 423 (M–Br), 503 (M+2H)

Example 2

Preparation of {1,3-bis-[N-(N'-methyl)imidazolidene-methyl]-benzene}-copper[II] bromide, $C_{15}H_{17}Br_2CuN_5$(× 2KBr)

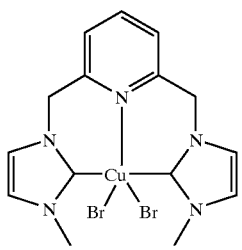

The bisimidazolium salt (131 mg, 0.31 mmol) is dissolved in 10 ml toluene under an argon atmosphere, and potassium tert-butylate (71 mg, 0.63 mmol) is added at 0° C. After 2 h copper(II) bromide (70 mg, 0.31 mmol) is added and the mixture is stirred for a further 12 h. The solvent is then removed in vacuo, and the product is obtained as a pale powder.

FD/MS: 330 (M–2Br, main component), 410 (M–Br), 490 (M+2H)

Example 3

Preparation of [N,N'-di(2-pyridyl)imidazolidene}-copper [II] bromide, $C_{13}H_{10}Br_2CuN_4$ (× KBr)

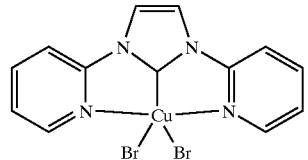

The imidazolium salt (92 mg, 0.31 mmol) is dissolved in 10 ml toluene under an argon atmosphere, and potassium tert-butylate (36 mg, 0.31 mmol) is added at 0° C. After 2 h copper(II) bromide (70 mg, 0.3 mol) is added and the mixture is stirred for a further 12 h. The solvent is then removed in vacuo, and the product is obtained as a pale powder.

FD/MS: 364 (M–Br, main component).

Example 4

Preparation of (N-benzyl-N'-methylimidazolidene)-copper [II] bromide, $C_{22}H_{24}Br_2CuN_4$ (× 2 KBr)

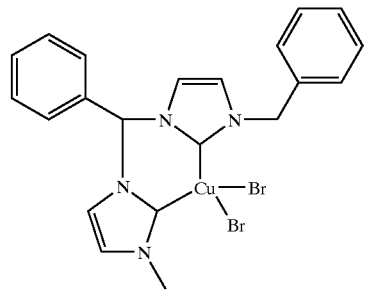

The imidazolium salt (300 mg, 1.2 mmol) is dissolved in 10 ml toluene under an argon atmosphere, and potassium tert-butylate (138 mg, 1.2 mmol) is added at 0° C. After 2 h copper(II) bromide (120 mg, 0.6 mmol) is added and the mixture is stirred for a further 12 h. The solvent is then removed in vacuo, and the product is obtained as a pale powder.

FD/MS: 316 (M–2Br, main component).

Example 5

Preparation of 4-nitrodiphenylamine catalyzed by Cu-carbene {1,3-[bis-(N-(N'-methyl)imidazelidene methyl]-5-methylbenzene}-copper(II)-bromide 288.9 g (3,090 mmol) aniline, 83.6 g (605 mmol) potash (preparation: ground for 60 sec at level 1 and 3×60 sec at level 2 of a laboratory mixer, the ground material being loosened by shaking after each 60 sec) and 157.6 g (1,000 mmol) 4-chloronitrobenzene and 9.42 g (16.2 mmol) {1,3-bis-[N-(N'-methyl)imidazolidene-methyl]-5-methylbenzene}-copper[II] bromide were initially introduced, while stirring, into a multi-necked round-bottomed flask with a KPG stirrer with a Teflon blade, Vigreux column, 55 ml water separator filled with xylene, blanketing with nitrogen, septum, heating mushroom and insulation. A red-brown suspension was formed and was heated up to the reflux temperature (stirrer approx. 400 rpm, very gentle stream of $N_2$). Thereafter, only a slight evolution of water initially occurred, but this increased in the course of the reaction and then remained constant at a low level (tot. approx. 6.9 ml). Sampling (unfiltered) took place every 30 minutes and the samples were analysed by means of HPLC (6-point calibration). After 390 minutes the experiment was ended. The boiling temperature of the mixture was about 192–199° C. during the entire duration of the experiment. A residual p-NCB value of 6.0 wt. % (corresponds to 84% conversion), a 4-NDPA content of 32.3 wt. %, a 4,4'-dinitrotriphenylamine content of 1.2% and a 4-NDPA/triarylamine ratio of 27 (corresponds to a yield of 81% 4-NDPA and 96% selectivity, based on the p-NCB) resulted here.

Result

| Sample | Sample [min] | p-NCB [wt. %] | 4-NDPA [wt. %] | Triple nucleus [wt. %] | Selectivity (NDPA/triple nucleus) |
|---|---|---|---|---|---|
| 1 | 30 | 23.5 | 8.7 | 0.00 | |
| 2 | 62 | 21.0 | 13.2 | 0.19 | 71.0 |
| 3 | 90 | 18.7 | 15.3 | 0.14 | 112.8 |
| 4 | 121 | 17.0 | 18.4 | 0.36 | 50.7 |
| 5 | 150 | 15.8 | 21.0 | 0.43 | 48.5 |
| 6 | 180 | 15.1 | 24.6 | 0.55 | 44.5 |
| 7 | 210 | 12.4 | 25.1 | 0.37 | 67.4 |
| 8 | 240 | 9.8 | 23.7 | 0.66 | 36.0 |
| 9 | 270 | 8.5 | 25.5 | 0.76 | 33.6 |
| 10 | 302 | 8.2 | 30.0 | 1.00 | 30.1 |
| 11 | 347 | 6.6 | 32.3 | 1.09 | 29.6 |
| 12 | 362 | 6.0 | 32.3 | 1.20 | 26.9 |

Example 6

Preparation of 4-nitrodiphenylamine catalysed by Cu-carbene {1,3-[bis-(N-(N'-methyl)imidazelidene methyl]-5-methylbenzene}-copper(II)-bromide in the presence of caesium.

288.9 g (3,090 mmol) aniline, 83.6 g (605 mmol) potash (preparation: ground for 60 sec at level 1 and 3×60 sec at level 2 of a laboratory mixer, the ground material being loosened by shaking after each 60 sec) and 157.6 g (1,000 mmol) 4-chloronitrobenzene and 0.50 g (3.78 mmol) Cs as an aqueous solution were initially introduced, while stirring, into a multi-necked round-bottomed flask with a KPG stirrer with a Teflon blade, Vigreux column, 55 ml water separator filled with xylene, blanketing with nitrogen, septum, heating mushroom and insulation. A red-brown suspension was formed and was heated up to the reflux temperature (stirrer approx. 400 rpm, very gentle stream of $N_2$). When the water had been removed from the circulation the mixture was cooled down to approx. 80° C. and 4.71 g (8.1 mmol) {1,3-bis-[N-(N'-methyl)imidazolidene-methyl]-5-methyl-benzene}-copper[II] bromide were added. After the mixture had been heated up again to the reflux temperature, only a slight evolution of water initially occurred, but this increased in the course of the reaction and then remained constant at a low level (tot. approx. 7.2 ml). Sampling (unfiltered) was carried out every 30 minutes and the samples were analysed by means of HPLC (6-point calibration). After 360 minutes the experiment was ended. The boiling temperature of the mixture was about 190–198° C. during the entire duration of the experiment. A residual p-NCB value of 6.2 wt. % (corresponds to 84% conversion), a 4-NDPA content of 33.9 wt. %, a 4,4'-dinitrotriphenylamine content of 1.92% and a 4-NDPA/triarylamine ratio of 17.7 (corresponds to a yield of 79% 4-NDPA and 95% selectivity, based on the p-NCB) resulted here.

Results

| Sample | Sample [min] | p-NCB [wt. %] | 4-NDPA [wt. %] | Triple nucleus [wt. %] | Selectivity (NDPA/triple nucleus) |
|---|---|---|---|---|---|
| 1 | 30 | 24.2 | 8.6 | 0.13 | 67.7 |
| 2 | 60 | 19.1 | 12.8 | 0.14 | 92.9 |
| 3 | 90 | 18.5 | 17.0 | 0.34 | 50.4 |
| 4 | 135 | 16.4 | 20.7 | 0.53 | 39.0 |
| 5 | 150 | 15.4 | 21.9 | 0.63 | 34.7 |
| 6 | 180 | 13.6 | 24.7 | 0.78 | 31.8 |
| 7 | 210 | 12.5 | 24.8 | 0.95 | 26.2 |
| 8 | 270 | 9.2 | 29.0 | 1.33 | 21.9 |
| 9 | 300 | 8.3 | 31.7 | 1.56 | 20.3 |
| 10 | 343 | 7.2 | 33.9 | 1.80 | 18.8 |
| 11 | 362 | 6.2 | 33.9 | 1.92 | 17.7 |

Example 7

Preparation of 4-aminodiphenylamine 250 ml water were added to the reaction mixture from example 5, after cooling to 105° C., and the mixture was stirred for 15 min at 80° C. and transferred to a separating funnel. After phase separation had taken place, 8 ml KOH, 25 ml salt water (from the aqueous phase of the condensation) and 4.5 g Raney nickel were added to the organic phase (500 ml) which had been separated off, the mixture was transferred to a hydrogenating autoclave and hydrogenation was carried out under a pressure of 10 bar of hydrogen in the course of 400 min, a temperature of 140° C. being reached. According to analysis by gas chromatography, 91% 4-aminodiphenylamine (based on the 4-nitrodiphenylamine employed) is obtained.

What is claimed is:

1. Process for the preparation of nitrodiphenylamines comprising reacting nitrohalogenobenzenes with anilines, a base and a catalyst of the formula (I)

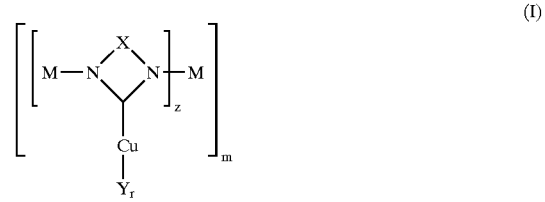

(I)

wherein

X is a 1,2-ethanediyl or 1,2-ethenediyl radical and

M can be identical or different and represents $C_1$–$C_{19}$-alkyl, $C_7$–$C_{19}$-aralkyl, $C_6$–$C_{18}$ aryl groups or $C_6$–$C_{19}$-heteroaryls having 1 to 3 nitrogen atoms, wherein two or more radicals M can be bridged in any desired manner by a covalent bridge or by an alkylidene bridge containing 1 to 4 carbon atoms or via an aryl or heteroaryl ring, Y represents halogen or a trifluoroacetyl, trifluoromethanesulfonyl, nonafluorobutanesulfonyl, cyanide, acetyl, fluorinated acetylacetonyl, nitrate, arylsulfonyl, oxinate, phosphate, carbonate or tetrafluoroborate radical, z represents 1, 2 or 3, m represents integers from 1 to 6 and r denotes 0, 1 or 2.

2. Process according to claim 1, wherein the base is chosen from the group consisting of bicarbonates, carbonates, methanolates, ethanolates, isopropylates, tert-butanolates, phosphates, fluorides, silazanes, hydrides and acetates of lithium, sodium, potassium and caesium.

3. Process according to claim 1, wherein the catalyst is prepared by deprotonation ligands of the formula (II)

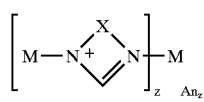
(II)

with a base and subsequently reacting with a copper compound of the formula (III)

(III)

wherein M, X, Y, z and r defined the same as in formula (I), and wherein "An" is an anion of an acid having a pKa value of 3 or less.

4. Process according to claim 3, wherein the catalyst of the formula (I) is prepared in situ.

5. Process according to claim 1, wherein the catalyst is selected from the group consisting of (N,N'-dimethylimidazolidene)-copper(II) bromide, (N,N'-dicyclohexylimidazolidene)-copper[II] bromide, [N,N'-di(2,4,6-trimethyl)phenylimidazolidene]-copper(II) bromide, [N,N'-di(2-pyridyl)imidazolidene]-copper[II] bromide, (N-benzyl-N'-methyl-imidazolidene)-copper[II] bromide, {1,3-bis-[N-(N'-methyl)imidazolidene-methyl]-5-methylbenzene}-copper[II] bromide, {1,3-bis-[N-(N'-methyl)imidazolidene-methyl]-5-methylbenzene}-copper[I] trifluoromethylsulfonate, {2,6-bis-[N-(N'-methyl)-imidazolidene-methyl]pyridine}-copper[II] bromide, {1,2-bis-[N-(N'-methyl)imidazolidene]-1,2-diphenylethane}-copper[II] bromide and {bis-[N-(N'-methyl)imidazolidene] methane}-copper[II] bromide, (N,N'-Dimethylimidazolidene)-copper(II) bromide and {1,3-[bis-(N-(N'-methyl)imidazolidenemethyl]-5-methylbenzene}-copper[II] bromide.

6. Process according to claim 1, wherein the nitrohalogenated benzenes are selected from the group consisting of 4-nitro-2-methylchlorobenzene, 4-nitro-3-methylfluorobenzene, 4-nitrochlorobenzene, 3-nitrochlorobenzene or 2-nitrochlorobenzene, 4-nitrochlorobenzene, 4-nitrophenyl-trifluoromethanesulfonic acid ester, 4-nitrophenylnonafluorobutane-sulfonic acid ester, 4-nitrophenyl carbamate and 4-nitrophenyltrifluoromethylsulfonic acid ester.

7. The process according to claim 1, wherein the aniline is a o-, m- or p-substituted aniline.

8. The process according to claim 7, wherein the substituted aniline is selected from the group consisting of vinylaniline, 4-tert.-butylaniline, p-anisidine, o-anisidine, o-toluidine, p-toluidine, anthranilic acid methyl ester, o-aminobenzonitrile, p-aminobenzonitrile and 4-ethylaniline.

9. Process for the preparation of aminodiphenylamine, wherein the nitrodiphenylamine produced according to claim 1 is hydrogenated without isolation.

* * * * *